US009147245B1

(12) United States Patent
Ghouti

(10) Patent No.: US 9,147,245 B1
(45) Date of Patent: Sep. 29, 2015

(54) METHOD, SYSTEM AND COMPUTER PROGRAM PRODUCT FOR BREAST DENSITY CLASSIFICATION USING FISHER DISCRIMINATION

(71) Applicants: King Fahd University of Petroleum and Minerals, Dhahran (SA); King Abdulaziz City for Science and Technology, Riyadh (SA)

(72) Inventor: Lahouari Ghouti, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 14/327,637

(22) Filed: Jul. 10, 2014

(51) Int. Cl.
*G06K 9/00* (2006.01)
*G06T 7/00* (2006.01)
*G06T 5/00* (2006.01)
*A61B 5/00* (2006.01)

(52) U.S. Cl.
CPC ............ *G06T 7/0012* (2013.01); *A61B 5/002* (2013.01); *A61B 5/0013* (2013.01); *A61B 5/4312* (2013.01); *A61B 5/7203* (2013.01); *A61B 5/7225* (2013.01); *A61B 5/7267* (2013.01); *G06T 5/002* (2013.01); *G06T 5/003* (2013.01); *G06T 7/0028* (2013.01); *G06T 7/0081* (2013.01); *G06T 7/0097* (2013.01); *A61B 2560/0475* (2013.01); *A61B 2576/02* (2013.01); *G06T 2200/28* (2013.01); *G06T 2207/10116* (2013.01); *G06T 2207/30068* (2013.01); *G06T 2207/30196* (2013.01); *G06T 2210/41* (2013.01)

(58) Field of Classification Search
CPC combination set(s) only.
See application file for complete search history.

(56) References Cited

U.S. PATENT DOCUMENTS

| 5,003,979 | A  | * | 4/1991  | Merickel et al. ............... 600/410 |
|-----------|----|---|---------|----------------------------------------|
| 6,405,065 | B1 |   | 6/2002  | Malin et al.                           |
| 7,266,407 | B2 | * | 9/2007  | Li et al. .......................... 600/430 |
| 7,680,312 | B2 | * | 3/2010  | Jolly et al. ..................... 382/128 |
| 7,684,596 | B2 | * | 3/2010  | Watson et al. ................. 382/128 |
| 8,086,049 | B2 |   | 12/2011 | Trifonov et al.                        |
| 8,094,904 | B2 | * | 1/2012  | Slabaugh et al. ............. 382/130 |
| 8,160,322 | B2 | * | 4/2012  | Dikmen et al. ................ 382/128 |
| 8,488,863 | B2 |   | 7/2013  | Boucheron                              |
| 2005/0177040 | A1 | * | 8/2005 | Fung et al. ..................... 600/407 |
| 2006/0083418 | A1 | * | 4/2006 | Watson et al. ................. 382/133 |
| 2008/0137969 | A1 | * | 6/2008 | Rueckert et al. .............. 382/224 |

(Continued)

OTHER PUBLICATIONS

C. Mata, et al., "Texture Descriptors applied to Digital Mammography". Jun. 5, 2008. 6 Pages. http://eia.udg.edu/~cmata/files/vibot2009.pdf.

(Continued)

*Primary Examiner* — Anand Bhatnagar
(74) *Attorney, Agent, or Firm* — Oblon, McClelland, Maier & Neustadt, L.L.P.

(57) ABSTRACT

A method for content-based image retrieval for the classification of breast density from mammographic imagery is described. The breast density is characterized through the Fisher linear discriminants (FLD) extracted from the Principal Component Analysis (PCA). Unlike PCA, the FLD provides a very discriminative representation of the mammographic images in terms of the breast density. Various exemplary methods, systems and computer program products are also disclosed.

10 Claims, 7 Drawing Sheets

(56) References Cited

U.S. PATENT DOCUMENTS

2010/0191141 A1    7/2010  Aberg
2012/0112751 A1*   5/2012  Littmann et al. ............. 324/322
2013/0059758 A1    3/2013  Haick et al.
2013/0272595 A1*  10/2013  Heine et al. .................. 382/132

OTHER PUBLICATIONS

C. Castella, et al., "Semiautomatic Mammographic Parenchymal Patterns Classification Using Multiple Statistical Features," Academic Radiology, 2007, 35 pages.

* cited by examiner

METHOD, SYSTEM AND COMPUTER PROGRAM PRODUCT FOR BREAST DENSITY CLASSIFICATION USING FISHER DISCRIMINATION

BACKGROUND OF THE INVENTION

1. Technical Field

The present invention relates to a method, a system and a computer program product for the classification of breast density from mammographic imagery. Specifically, the invention relates to an automated content-based image retrieval (CBIR) method, system and computer program product for the classification of breast density in mammogram images.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In a study covering data population from 1975-1988, the US National Cancer Institute (NCI) estimates that the overall lifetime risk for developing invasive breast cancer is approximately one in eight (approximately 12.6 percent) among American women (U.S. Cancer Statistics Working Group. United States Cancer Statistics: 1999-2008 Incidence and Mortality Web-based Report. Atlanta: U.S. Department of Health and Human Services, Centers for Disease Control and Prevention and National Cancer Institute; 2012. Available at: www.cdc.gov/uscs—incorporated herein by reference in its entirety). Aiming to increase the survival time for women with breast cancer, mass-screening mammography programs are developed and adopted as an effective method. The integration of Computer-Aided Detection (CAD) tools with these screening programs is an interesting avenue worth exploring. Recent advances in CAD techniques and systems have focused on the detection of calcifications and the detection of mammographic masses. Although various degrees of success have been achieved in the above-mentioned detection problems, the accurate identification of breast cancer from digital mammogram images still remain a challenging and daunting task. Based on mammogram images, the mammographic appearance of the breast widely varies which constitutes a real challenge for the radiologist exploring and/or interpreting a benign mammogram.

There exist various types of radiographically-visible density including: 1) Ducts; 2) Lobular elements; and 3) Fibrous connective tissue. The fibrous connective tissue is further classified into: 1) Intralobular tissue; and 2) Extralobular tissue. The high variability in breast density reported from mammograms is mainly due to the extralobular tissue.

The interpretation of a mammogram images depends heavily on the breast density. In fact, the breast density affects the early detection of malignancy and large cancers especially in case of considerable density. In such cases, the mammogram background is not uniform and, therefore, it is very difficult to locate ill-defined cancers. The American College of Radiology (ACR) Breast Imaging Reporting and Data System (BIRADS) adopts a standard breast density classification system. In this system, the breast density is classified into four (04) major categories according to the recommendations of the American College of Radiology (ACR) Breast Imaging Reporting and Data System (BIRADS) (U.S. Cancer Statistics Working Group. United States Cancer Statistics: 1999-2008 Incidence and Mortality Web-based Report. Atlanta: U.S. Department of Health and Human Services, Centers for Disease Control and Prevention and National Cancer Institute; 2012. Available at: www.cdc.gov/uscs—incorporated herein by reference in its entirety): 1) Extremely dense; 2) Heterogeneously dense; 3) Fat with some fibroglandular tissue; and 4) Predominantly fat.

FIG. 1 illustrates examples of the above-mentioned breast densities.

It has been a widely accepted fact that dense tissue indicates a much higher risk of developing breast cancer than a fatty tissue (D. Kopans, Breast imaging, 3rd Edition, Lippincott-Raven, Philadelphia, 2006—incorporated herein by reference in its entirety). On the other hand, the presence of breast cancer is often masked in a mammogram having a dense tissue which increases the likelihood of missing the presence of breast cancer. Therefore, the challenge is doubled for women by being at higher risk of the disease and higher risk of cancer misdiagnosis by the mammographic approach. However, a recent study published in the Journal of the National Cancer Institute (U.S. Cancer Statistics Working Group. United States Cancer Statistics: 1999-2008 Incidence and Mortality Web-based Report. Atlanta: U.S. Department of Health and Human Services, Centers for Disease Control and Prevention and National Cancer Institute; 2012—incorporated herein by reference in its entirety. Available at: www.cdc.gov/uscs) revealed that, among women with breast cancer, those with fat breasts do not have a lower risk of dying of the disease than those with denser breasts. In this study, 9000 breast cancer patients were followed for an average period of 6½ years. During that time, 889 of these women died of breast cancer. There was no difference in the death rate of women with the densest breasts on mammography versus those with less dense (fattier) breasts. In some U.S. states, mammography facilities are required by state law to notify their patients if they have dense breasts. In such situations, patients are advised to inquire about whether they should undergo additional screening with ultrasound or MRI. This additional screening may detect breast cancer cases missed by the mammography procedure. However, it should be noted that additional screening will also greatly increase the likelihood of false alarms leading to unnecessary biopsies and the overall cost of screening approach.

Automated classification of breast density can be classified into: 1) Matrix factorization; 2) Global histogram; and 3) Texture analysis methods. Matrix factorization techniques factorize the mammogram images into a product of several factor images according to specific constraints. Consequently, the mammographic images, known for their high dimensionality, undergo a drastic dimensionality reduction where only dominant features are kept. Oliver et al. (A. Oliver, X. Lado, E. Perez, J. Pont, J. Denton, E. Freixenet, and J. Marti., "Statistical approach for breast density segmentation. Journal of Digital Imaging," vol. 23, no. 5, pp. 55-65, 2009—incorporated herein by reference in its entirety) proposed a two-class breast density classification. Image segmentation is used as a pre-processing step. Then, features are extracted using principle component analysis (PCA) and linear discriminant analysis (LDA) techniques to classify the mammogram images into fatty and dense types. LDA is also sometimes known as Fisher Linear Discriminant (FLD). Features extracted using 2D-PCA are proposed by DeOlivera et al. (J. E. E. de Oliveira and A. de Araujo. Mammosyslesion: A content-based image retrieval system for mammographies," in 17th International Conference on Systems, Signals and Image Processing (IWSSIP 2010), pp. 408-411, 2010—incorporated herein by reference in its entirety) to build a two-class (fatty and dense) content-based image retrieval (CBIR) system. A support vector machine (SVM) with Gaussian kernels classifies image features represented by the first four principle components (PC). Reported results indicate that 2D-PCA outperforms the standard PCA in terms of classification accuracy. Using the same features, proposed in DeOlivera et al. (J. E. E. de Oliveira and A. de Araujo. Mammosyslesion: A content-based image retrieval system for mammographies," in 17th International Conference on Systems, Signals and Image Processing (IWSSIP 2010), pp. 408-411, 2010—incorporated herein by reference in its entirety), Thomas et al. (T. M. Deserno, M. Soiron, J. E. E. de Oliveira, and A. de Araujo, "Towards computer-aided diagnostics of screening mammography using content-based image retrieval," in 24th Conference on Graphics, Patterns and Images (Sibgrapi 2011), pages 1754-1760, 201—incorporated herein by reference in its entirety) consider 4 density classes according to the BI-RADS lexicon using a similar classifier. DeOliveira et al. (J. E. E. de Oliveira, G. Camara-Chavez, A. de Araujo, and T. M. Deserno, "Mammosvd: A content-based image retrieval system using a reference database of mammographies," in 22nd IEEE International Symposium on Computer-Based Medical Systems, pp. 1-4, 2009—incorporated herein by reference in its entirety) propose a CBIR system, called MammoSVD, where image features are extracted using the singular value decomposition (SVD) algorithm. It is noteworthy that MammoSVD system is a binary classifier (fatty and dense tissue) based on an SVM learning machine. The SVD-based features provide a good characterization of the mammographic texture. MammoSVD system achieves 90% classification accuracy. In DeOliveira et al. (J. E. E. de Oliveira, G. Camara-Chavez, A. de Araujo, and T. M. Deserno, "Content-based image retrieval applied to BI-RADS tissue classification in screening," World Journal of Radiology, vol. 3, no. 1, pp. 24-31, 2011—incorporated herein by reference in its entirety), a 4-class model, called MammoSVx is proposed with features are represented using the largest 25 singular values of the SVD decomposition of the mammogram images. Using an SVM learning model with polynomial kernel against a mammographic database containing 10000 images, a classification accuracy of 82.14% is achieved by MammoSVx.

Disclosed embodiments of the present invention relate to a method, a system and a computer program product for the classification of breast mammographic images according to the breast type identified on the basis of the underlying texture of the breast which is highly correlated with the breast density. Then, based on this classification, the disclosed method, system or computer program product generates a new mammogram image which is automatically categorized into one of the density classes. This automation mitigates subjectivity introduced by the manual process carried out by radiologists. Moreover, further image handling and process is applied based on this classification. From an image processing viewpoint, processing algorithms are used according to the breast density of the underlying mammogram images. In the same time, "hard" cases can be singled out for further processing or double screening as per the BIRADS recommendations. (G. L. Gierach, L. Ichikawa, K. Kerlikowske, L. A. Brinton, G. N. Farhat, P. M. Vacek, D. L. Weaver, C. Schairer, S. H. Taplin S H and M. E. Sherman, "Relationship between mammographic density and breast cancer death in the breast cancer surveillance consortium," Journal of Natl. Cancer Inst., Vol. 104, No. 16, pp 1218-1227, August 2012—incorporated herein by reference in its entirety).

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

According to a first aspect, the present invention provides a computer-implemented method, system and computer program product for classifying breast density from mammographic imagery using content-based image retrieval (CBIR) comprising (a) removing noise and enhancing contrast of digital mammogram images of a patient; (b) segmenting the mammogram images to produce extracted regions of interest (ROI); (c) grouping the extracted regions of interest into a large mammogram image; (d) decomposing the large mammogram image by principal component analysis (PCA); and (e) classifying the large mammogram image according to breast density with Fisher Linear Discriminant (FLD).

In one embodiment, the PCA decomposition analysis may use Formula II:

$$E[\text{Mammo}_{db}^T \text{Mammo}_{db}] = [UDV^T] \qquad \text{Formula II}$$

In another embodiment, the PCA decomposition analysis may use Formula III:

$$\text{Proj} = U^T \Omega \qquad \text{Formula III}$$

In another embodiment, the large mammogram image is represented as a column vector and stored as a stacked column vector in the mammogram image database.

In yet another embodiment, the FLD classification in the disclosed method performs in a space where breast density classes are well separated where the inter-class margins and intra-class margins are minimized by using Formula IV to maximize the ratio of an inter-class scatter and an intra-class scatter. The inter-class maximization is achieved by an optimization procedure and achieved ratios are data dependent:

$$T_{FLD} = \underset{T}{\text{argmax}} \frac{|T^T S_B T|}{T^T S_W T} = [t_1 \; t_2 \; \ldots \; t_K]^T \qquad \text{Formula IV}$$

In another embodiment, the BI-RADS breast density classification system may be adopted into the disclosed method.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
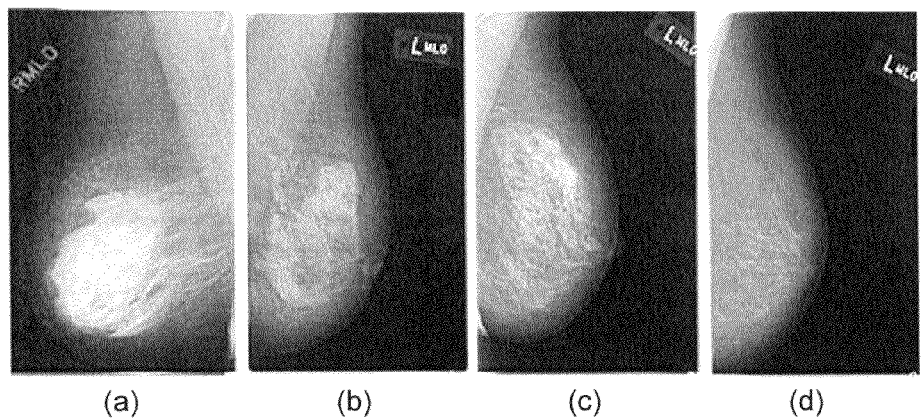
FIG. 1 is a series of mammogram images illustrating four breast density classifications: (a) Extremely dense; (b) Heterogeneously dense; (c) Fat with some fibroglandular tissue; and (d) Predominantly fat.

Referring now to the drawings, wherein like reference numerals designate identical or corresponding parts throughout the several views. In medical content-based information retrieval (Med-CBIR) systems, the access to information is performed by the visual attributes extracted from images. The definition of a set of features, capable to describe effectively each region contained in an image, is one of the most complex tasks in the analysis of images. In addition, the process of characterization affects all the subsequent process of a Med-CBIR system (U.S. Cancer Statistics Working Group. United States Cancer Statistics: 1999-2008 Incidence and Mortality Web-based Report. Atlanta: U.S. Department of Health and Human Services, Centers for Disease Control and Prevention and National Cancer Institute; 2012. Available at: www.cdc.gov/uscs—incorporated herein by reference in its entirety). An image can be numerically represented by a feature vector, which should reduce the dimensionality of the image and emphasize aspects of this image (D. Kopans, Breast imaging, 3rd Edition, Lippincott-Raven, Philadelphia, 2006—incorporated herein by reference in its entirety)

The Med-CBIR system as disclosed herein is based on breast density classification using features extracted from the Fisher Linear Discriminant (FLD) representation of the main texture features retained using the principal component analysis (PCA).

FLD is noted for an especially favorable combination of satisfactory classification accuracy coupled with consistency across different data sets and a low training. In FLD, directions in property space are defined along which the inter-class variance is maximized and the intra-class variance is minimized. In other words, directions in property space are sought which separate the class centers as widely as possible while simultaneously representing each class as compactly as possible. When there are two classes, there is a single discriminant direction (U.S. Pat. No. 8,086,049 B2—incorporated herein by reference in its entirety).

Figure 2:
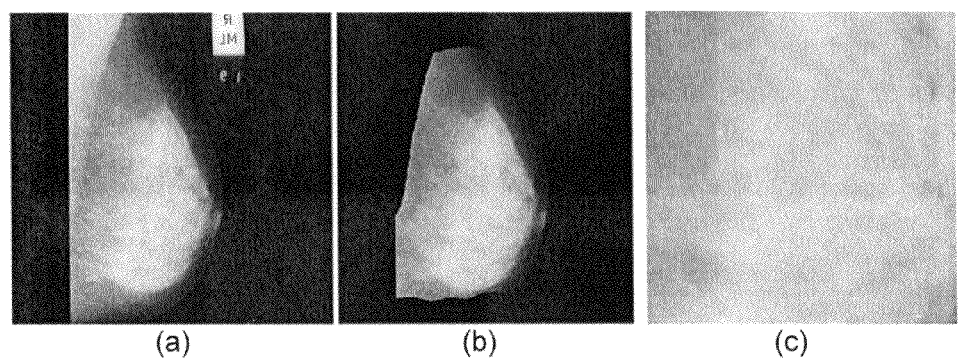
FIG. 2 is a series of images illustrating the pre-processing and segmentation process of the disclosed Med-CBIR system: (a) A raw mammogram image; (b) A pre-processed and segmented sample of the mammogram image in 2(a); and (c) An extracted region of interest (ROI) area of the sample in 2(b).

In one embodiment, the disclosed system consists of 3 main building blocks:

1. Pre-processing and segmentation: The pre-processing step is used for successful and error-free mammographic interpretation. This step includes noise removal and contrast enhancement. Next, the segmentation step aims to separate the breast from other objects in the mammogram image with a minimum loss of breast tissue (C. Mata, J. Freixenet, X., Llado and A. Oliver, "Texture descriptors applied to digital mammography,"—incorporated herein by reference in its entirety. Available online at http://eia.udg.edu/~cmata/files/vibot2009.pdf). In screening mammography, both head-to-foot (craniocaudal, CC) view and angled side-view (mediolateral oblique, MLO) images of the breast are taken. During segmentation, the pectoral muscle, visible in MLO views, is separated apart enabling the extraction of the image region of interest (ROI). In one embodiment, the extracted ROIs contain 300×300 pixels. A sample mammographic image and its pre-processed sample are shown in FIG. 2. As shown in FIG. 2, pre-processing and segmentation have significantly improved the visual quality of the image prior to inspection by radiologists.

Figure 3:
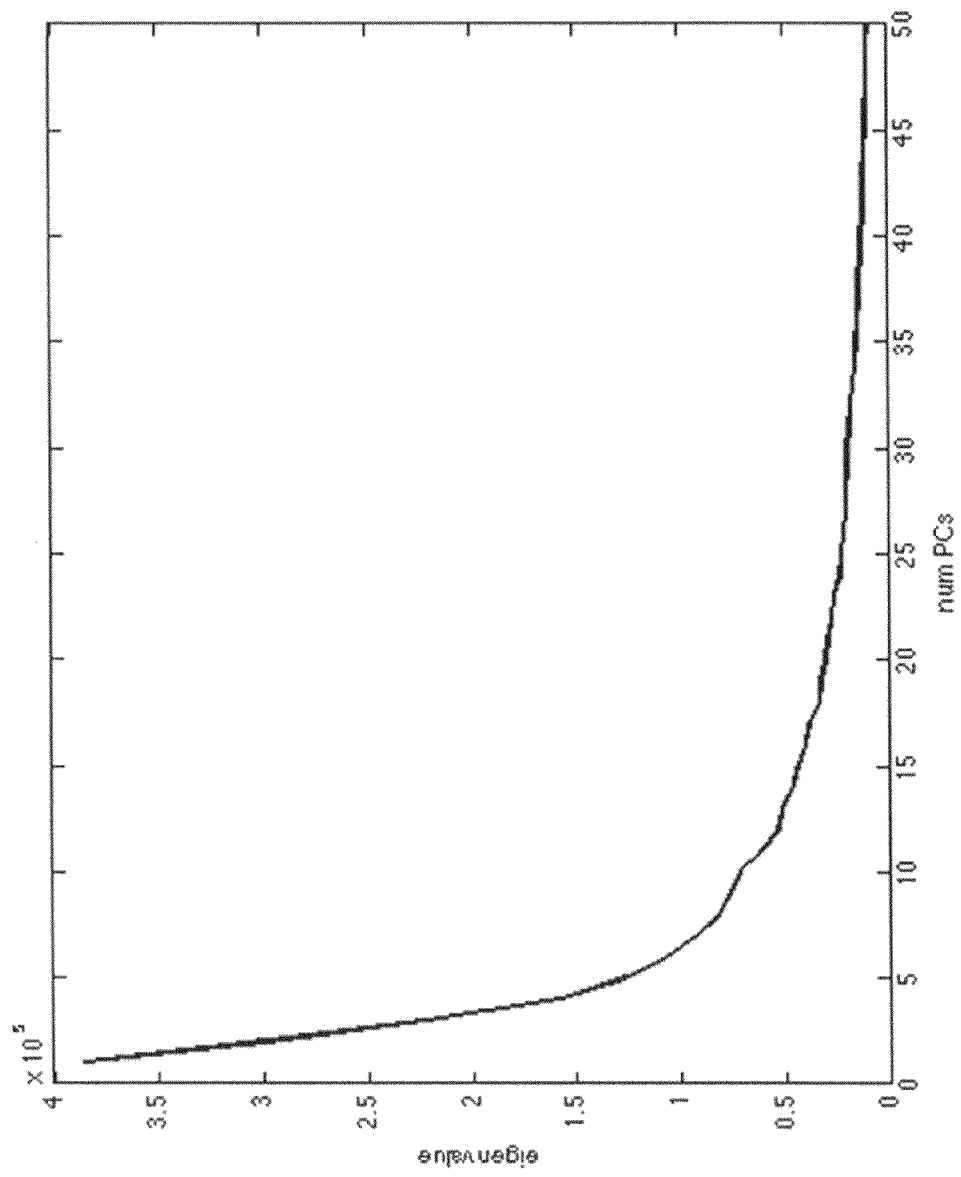
FIG. 3 is a graph illustrating a typical drop in eigenvalue energy during a data reduction process.

2. Feature extraction and selection: Mammogram images, having the same density annotation, are grouped into a large mammogram image which is decomposed using the principle component analysis (PCA) algorithm. During this patch-based feature or data reduction process, features are extracted by maximizing the data variance in order to retain only the first few factors. The number of retained features is automated using a cutoff defined by a drastic drop in the energy of the eigenvalues. This eigenvalue drop is directly related to the quality of the reconstructed image that usually retains up to 80% of the original image. FIG. 3 illustrates a typical drop in the eigenvalue energy.

Figure 4:
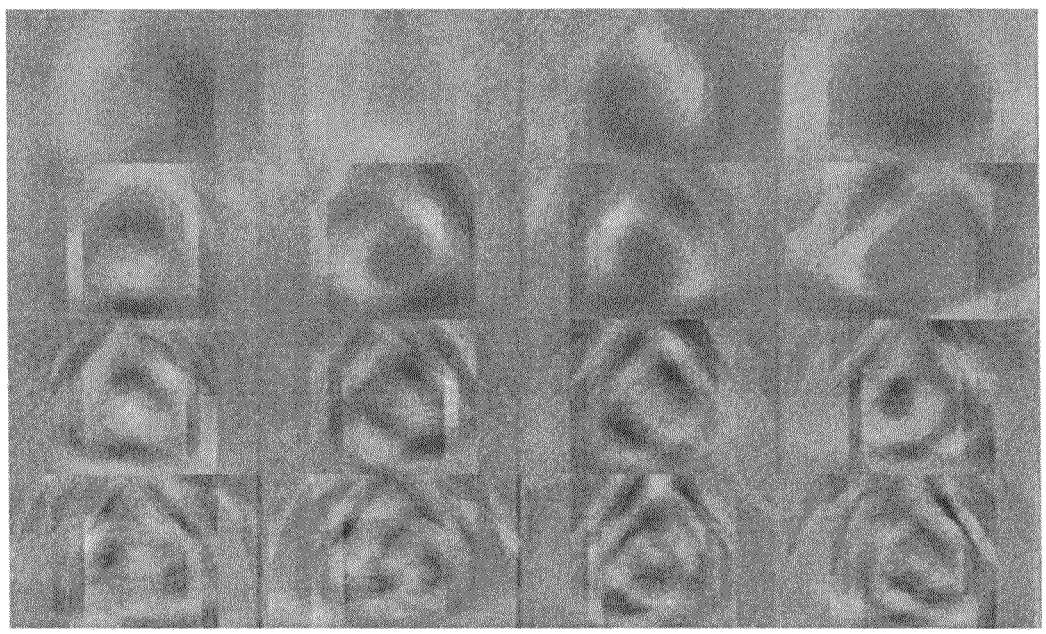
FIG. 4 is an image of the principle component analysis (PCA) decomposition using the first 16 bases.

3. The PCA decomposition efficiency is illustrated in FIG. 4 where only the first 16 PCs are shown. Breast density class discrimination is guaranteed by the use of the Fisher Linear Discriminant (FLD) processing.

4. Machine learning-based classification: Given their universal classification capabilities, support vector machines (SVM) are used to classify the breast density classes (binary or multi class). As such, a Med-CBIR system based on the breast density categorization is used for classification. The SVM classifier finds the linear decision boundary (or hyperplane) that successfully separates data pertaining to two given classes. Moreover, this hyperplane maximizes the separating distance between the two classes. A higher classification performance is achieved by greater separating distance. For example, maximum-margin classifiers outperform neural-based ones by attaining 5 to 10% improvement in classification accuracy (C. M. Bishop, "Pattern recognition and machine learning," Vol. 1, New York: Springer, 2006—incorporated by reference herein in its entirety).

Figure 5:
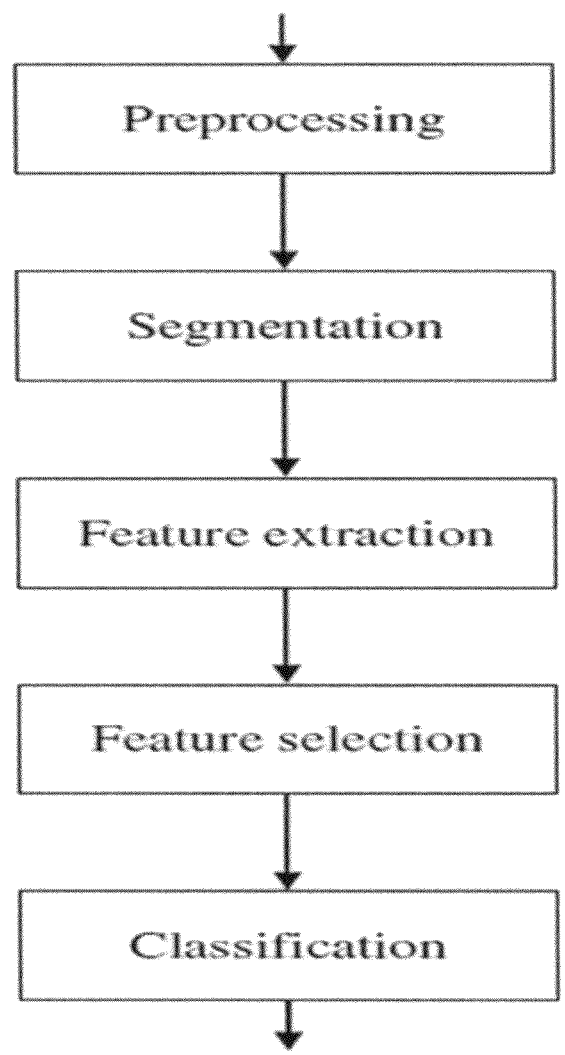
FIG. 5 is a flow chart illustrating the steps in the Med-CBIR system using breast density classification.

The Med-CBIR system disclosed in the present invention is illustrated in FIG. 5.

Figure 6:
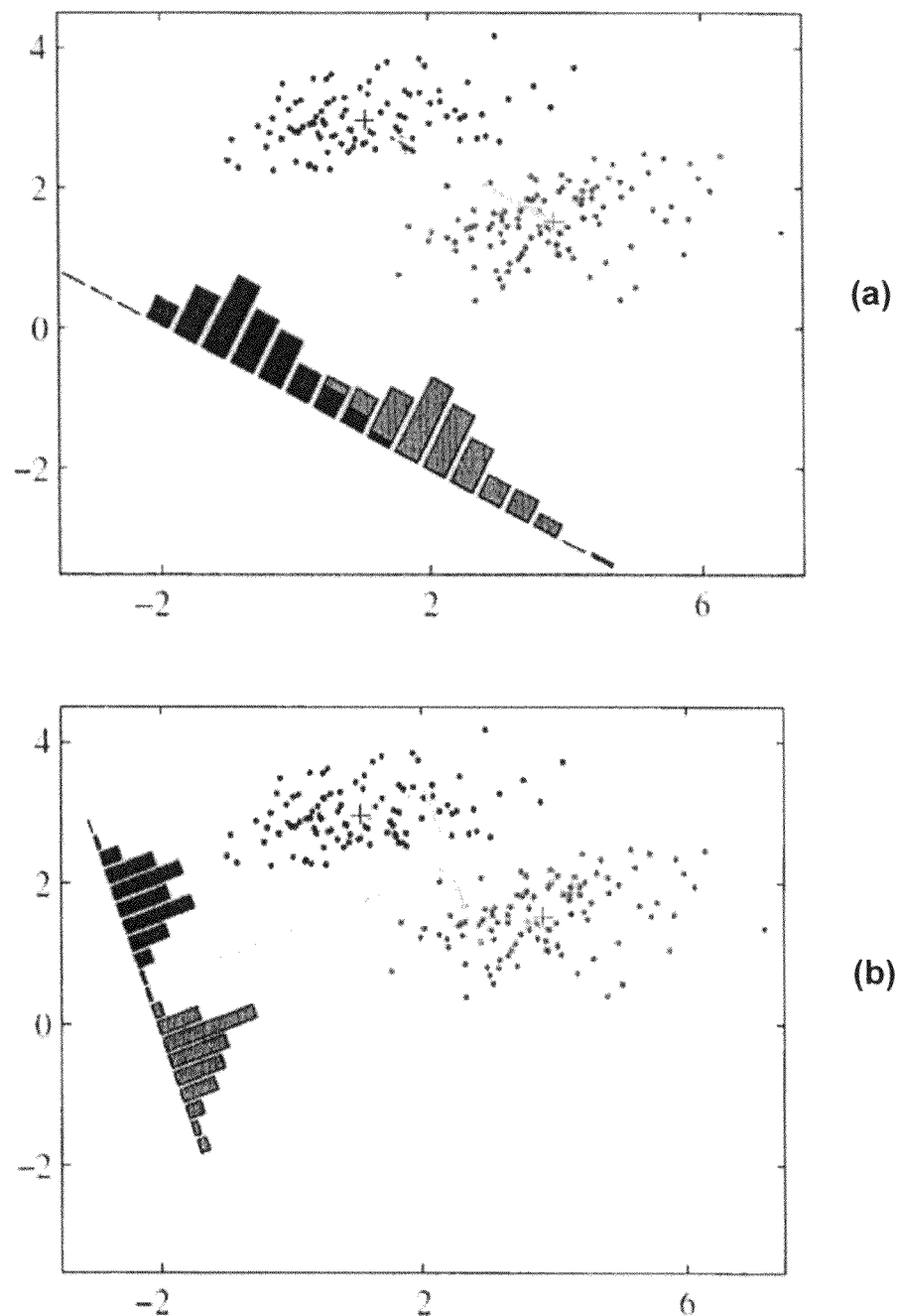
FIG. 6 is a graph illustrating discrimination of BI-RADS breast density classes in (a) PCA; and (b) Fisher Linear Discriminant (FLD).

In one embodiment, the Fisher's Linear Discriminant (FLD) classification technique is used to classify mammogram images according to their breast densities. FLD, which is also known as LDA (Linear Discriminant Analysis) finds an optimal subspace where classification is performed while maximizing the ratio of the between or inter-class scatter and the within or intra-class scatter. In an exemplary embodiment, the breast density classification is performed in a space where the standard BI-RADS breast density classes are well separated with the inter-class margins maximized and intra-class margins minimized, as depicted in FIG. 6.

In one embodiment, a mammogram image database, Mammo$_{db}$, is constructed where each mammogram image is represented by a column vector such as:

$$\text{Mammo}_{db} = \begin{bmatrix} \vdots & & \vdots \\ m_1 & \vdots & m_L \\ \vdots & & \vdots \end{bmatrix} \quad \text{Formula I}$$

where each mammogram image, $m_i$, is stored as a stacked column vector. The database contains L mammogram images. A better representation of the mammographic data base is obtained using the PCA decomposition of the covariance matrix of $\text{Mammo}_{db}$ using:

$$E[\text{Mammo}_{db}^T \text{Mammo}_{db}] = [UDV^T] \quad \text{Formula II}$$

where U and V represent the left and right eigenvectors associated with the eigenvalues stored in the diagonal matrix D.

Using U as the basis, each mammographic image, $m_i$, is projected into the feature space as follows:

$$\text{Proj} = U^T \Omega \quad \text{Formula III}$$

where $\Omega$ and Proj represent the original and subspace-projected mammographic images, respectively.

Figure 7:
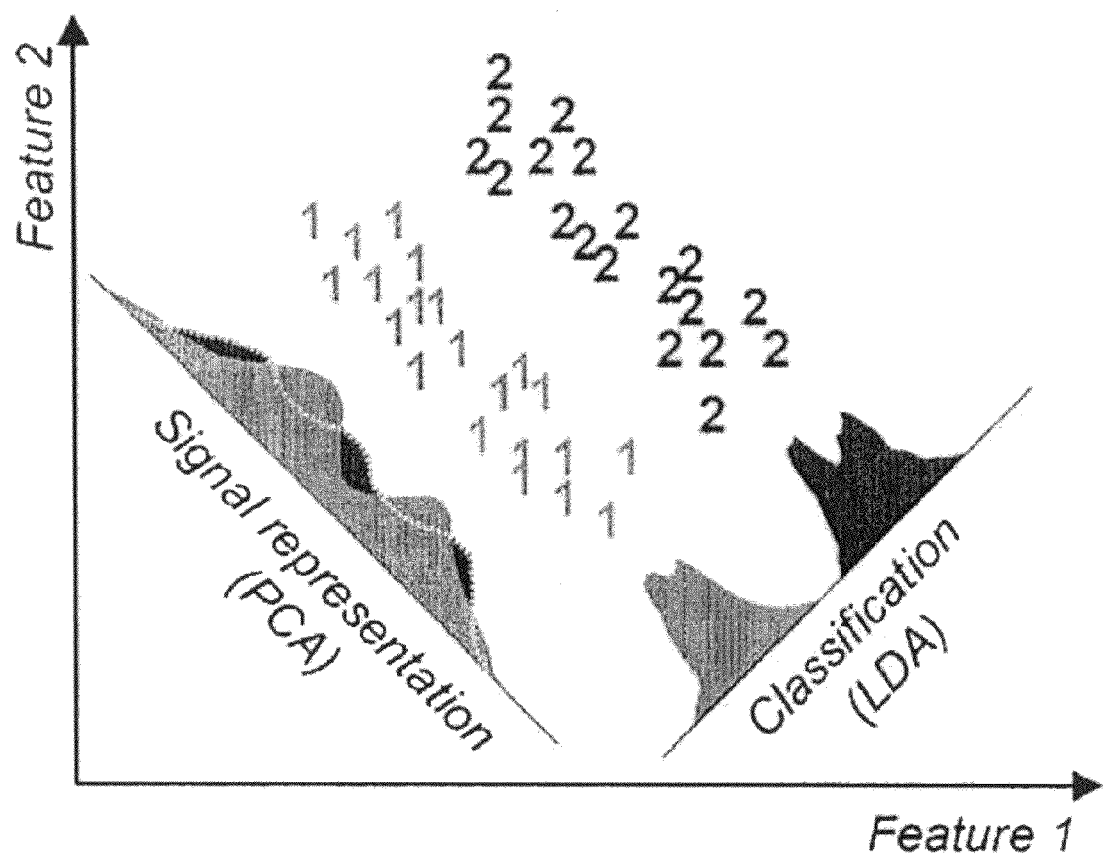
FIG. 7 is a graph illustrating the difference between PCA and FLD in terms of class discriminality.

The projected images contained in Proj may suffer from poor class discriminality, making it very hard to distinguish between mammographic images pertaining to different breast density classes. In this case, FLD is applied to Proj to find an optimal subspace where the ratio of the between or inter-class scatter, $S_B$, and the within or intra-class scatter, $S_W$, is maximized as follows:

$$T_{FLD} = \underset{T}{\arg\max} \frac{|T^T S_B T|}{T^T S_W T} = [t_1 \; t_2 \; \ldots \; t_K]^T \quad \text{Formula IV}$$

where the size of $T_{FLD}$ is K×M (K≤M) and $\{t_i | i=1, 2, \ldots, K\}$ is the set of discriminant vectors of $S_B$ and $S_W$ corresponding to the largest P generalized eigenvalues. In one embodiment, P corresponds to the number of breast density classes adopted in the BI-RADS system. FIG. 7 illustrates the difference between PCA and FLD in terms of class discriminality. More specifically, FLD has been successfully applied in deployed systems including face-based biometric systems where improvement of 19% recognition accuracy was achieved (P. N. Belhumeur, J. P. Hespanha, and D. Kriegman, "Eigenfaces vs. Fisherfaces: Recognition using class specific linear projection," IEEE Transactions on pattern Analysis and machine Intelligence, Vol. 19, No. 7, 711-720, 1997—incorporated by reference herein in its entirety).

Figure 8:
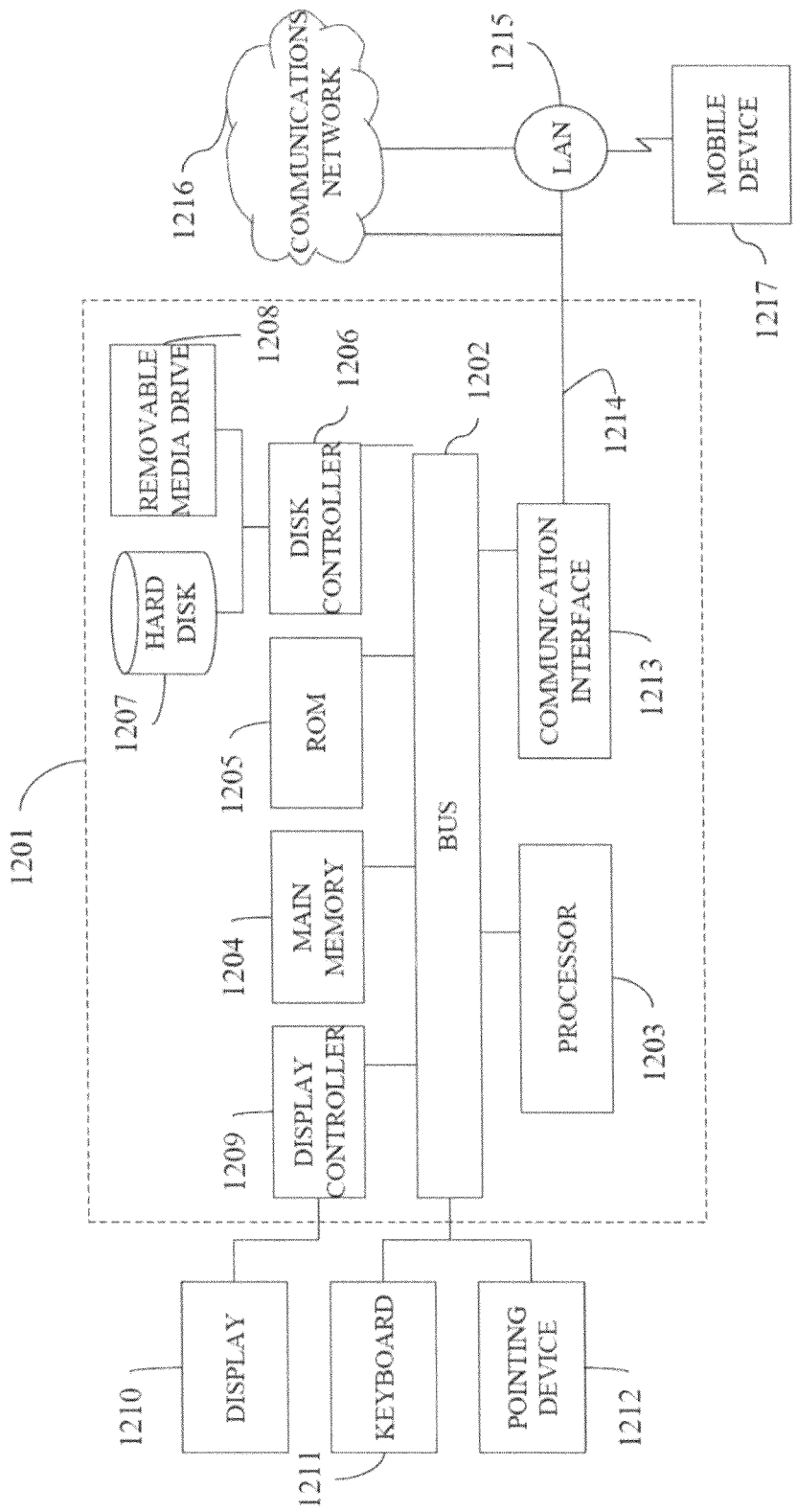
FIG. 8 is a schematic diagram of an exemplary computing system capable of implementing the various exemplary methods described herein.

FIG. 8 illustrates a computer system 1201 upon which an embodiment of the present invention may be implemented. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A computer-implemented method for classifying breast density from mammographic imagery using content-based image retrieval comprising:
   (a) pre-processing one or more digital mammogram images of a patient to remove noise and enhance contrast;
   (b) segmenting the one or more digital mammogram images to produce one or more extracted regions of interest and saving the one or more extracted regions of interest in computer memory;
   (c) grouping the one or more extracted regions of interest saved in memory to produce a large mammogram image;
   (d) decomposing, with a processor of a computer, the large mammogram image by principal component analysis (PCA) in a mammogram image database; and
   (e) classifying, with a processor of a computer, the large mammogram image according to breast density with Fisher Linear Discriminant (FLD) in the mammogram image database.

2. The method of claim 1, wherein step (d) decomposes a covariance matrix of the mammogram image database with Formula II:

$$E[\text{Mammo}_{db}^T \text{Mammo}_{db}] = [UDV^T];$$

and projects the large mammogram image into a feature space with Formula III:

$$\text{Proj} = U^T \Omega;$$

wherein:
Mammo$_{db}$ represents the mammogram image database;
U and V represent the left and right eigenvectors, respectively, associated with the eigenvalues stored in diagonal matrix D;
Ω and Proj represent the original and projected large mammogram image, respectively.

3. The method of claim 1, wherein the mammogram image database represents the large mammogram image as a column vector and stores the large mammogram image as a stacked column vector in memory.

4. The method of claim 1, wherein step (e) is performed in a space where breast density classes are wherein inter-class margins are maximized and intra-class margins are minimized by using Formula IV to maximize the ratio of an inter-class scatter and an intra-class scatter:

$$T_{FLD} = \underset{T}{\mathrm{argmax}}\frac{|T^T S_B T|}{T^T S_W T} = [\, t_1 \ \ t_2 \ \ \ldots \ \ t_K \,]^T.$$

wherein:
the size of $T_{FLD}$ is K×M (K≤M) and $\{t_i | i=1, 2, \ldots, K\}$ is the set of discriminant vectors of $S_B$ and $S_W$ corresponding to the largest P generalized eigenvalues.

5. The method of claim 4, wherein the breast density classes are according to the BI-RADS classification system.

6. A non-transitory computer-readable storage medium having computer-readable instructions thereon which when executed by a computer case the computer to perform a computer-implemented method for classifying breast density from mammographic imagery using content-based image retrieval comprising:
(a) pre-processing one or more digital mammogram images of a patient to remove noise and enhance contrast;
(b) segmenting the one or more digital mammogram images to produce one or more extracted regions of interest and saving the one or more extracted regions of interest in computer memory;
(c) grouping the one or more extracted regions of interest to produce a large mammogram image;
(d) decomposing, with a processor of a computer, the large mammogram image by principal component analysis in a mammogram image database (PCA); and
(e) classifying, with a processor of a computer, the large mammogram image according to breast density with Fisher Linear Discriminant (FLD) in the mammogram image database.

7. The computer-readable storage medium of claim 6, wherein step (d) decomposes a covariance matrix of the mammogram image database with Formula II:

$$E[\mathrm{Mammo}_{db}^T \mathrm{Mammo}_{db}] = [UDV^T];$$

and projects the large mammogram image into a feature space with Formula III:

$$\mathrm{Proj} = U^T \Omega;$$

wherein:
$\mathrm{Mammo}_{db}$ represents the mammogram image database;
U and V represent the left and right eigenvectors, respectively, associated with the eigenvalues stored in diagonal matrix D;
$\Omega$ and Proj represent the original and projected large mammogram image, respectively.

8. The computer-readable storage medium of claim 6, wherein the mammogram image database represents the large mammogram image as a column vector and stores the large mammogram image as a stacked column vector in memory.

9. The computer-readable storage medium of claim 6, wherein step (e) is performed in a space where breast density classes are wherein inter-class margins are maximized and intra-class margins are minimized by using Formula IV to maximize the ratio of an inter-class scatter and an intra-class scatter:

$$T_{FLD} = \underset{T}{\mathrm{argmax}}\frac{|T^T S_B T|}{T^T S_W T} = [\, t_1 \ \ t_2 \ \ \ldots \ \ t_K \,]^T.$$

wherein:
the size of $T_{FLD}$ is K×M (K≤M) and $\{t_i | i=1, 2, \ldots, K\}$ is the set of discriminant vectors of $S_B$ and $S_W$ corresponding to the largest P generalized eigenvalues.

10. The method of claim 9, wherein the breast density classes are according to the BI-RADS classification system.

\* \* \* \* \*